(12) United States Patent
Cao et al.

(10) Patent No.: US 12,257,349 B2
(45) Date of Patent: Mar. 25, 2025

(54) COMPARTMENTED HARD SHELL CAPSULE AND APPARATUS AND METHOD FOR FORMING, FILLING, AND ENCAPSULATING A COMPARTMENTED HARD SHELL CAPSULE

(71) Applicants: Karl Wei Cao, Vancouver (CA); Hu Cao, Taiyuan (CN)

(72) Inventors: Karl Wei Cao, Vancouver (CA); Hu Cao, Taiyuan (CN)

( * ) Notice: Subject to any disclaimer, the term of this patent is extended or adjusted under 35 U.S.C. 154(b) by 281 days.

(21) Appl. No.: 17/351,190

(22) Filed: Jun. 17, 2021

(65) Prior Publication Data

US 2022/0401371 A1 Dec. 22, 2022

(51) Int. Cl.
*A61K 9/48* (2006.01)
*A61J 3/07* (2006.01)
*B29C 41/14* (2006.01)

(52) U.S. Cl.
CPC ............ *A61K 9/4808* (2013.01); *A61J 3/071* (2013.01); *A61J 3/077* (2013.01); *A61K 9/4833* (2013.01); *B29C 41/14* (2013.01)

(58) Field of Classification Search
CPC .......... A61K 9/4808; A61J 3/071; A61J 3/077
See application file for complete search history.

(56) References Cited

U.S. PATENT DOCUMENTS

| | | | |
|---|---|---|---|
| 4,534,467 A * | 8/1985 | Rathbun | A61J 3/071 426/138 |
| 7,445,795 B2 | 11/2008 | Bakhshaee et al. | |
| 7,670,612 B2 | 3/2010 | Miller | |
| 8,361,497 B2 | 1/2013 | Miller | |
| 9,456,990 B2 * | 10/2016 | McInnes | A61J 3/071 |

FOREIGN PATENT DOCUMENTS

| CN | 208574031 U | * 3/2019 | A61K 9/48 |
|---|---|---|---|
| CN | 208958833 U | * 6/2019 | A61K 9/48 |

* cited by examiner

*Primary Examiner* — Blessing M Fubara
(74) *Attorney, Agent, or Firm* — WILLIAMS INTELLECTUAL PROPERTY (57) ABSTRACT

A compartmented hard shell capsule for containing active formulations, and methods and apparatuses for forming, filling and encapsulating the compartmented hard shell capsules. The compartmented hard shell capsule includes a cap portion and a body portion. The cap portion has a hollow cavity defining a cap chamber. The body portion can be removably inserted into the cap portion. The body portion has an open end, a closed end and a sidewall defining a hollow cavity and a serrated edge along the open end. The serrated edge may be folded over to form a barrier to enclose the body portion, thereby creating a body chamber that is separate from the cap chamber when the body portion is inserted into the cap portion. The methods for filling and encapsulating the compartmented hard shell capsules can be completed in one continuous process, which increases cost-effectiveness for use of the compartmented hard shell capsules.

6 Claims, 7 Drawing Sheets

COMPARTMENTED HARD SHELL CAPSULE AND APPARATUS AND METHOD FOR FORMING, FILLING, AND ENCAPSULATING A COMPARTMENTED HARD SHELL CAPSULE

TECHNICAL FIELD

The disclosure relates generally to a compartmented hard shell capsule and an apparatus for and a method of forming, filling and encapsulating compartmented hard shell capsules and more particularly to compartmented hard shell capsules made of any film forming material for oral dosage of pharmaceuticals, vitamins, food and diagnostic products.

BACKGROUND

Oral administration is a preferred delivery method for active ingredients in pharmaceuticals, nutrition and other therapeutic preparations due to its low cost, convenience and the large absorption area of the digestive system. Tablets and capsules are generally the most common forms of oral delivery. The hard capsule is one of the most preferred delivery methods by patients because it is easy to swallow, neutral in taste and smell and easier for patient compliance.

Hard shell capsules are traditionally made by a dipping process that forms two parts, a cap part and a body part, each with open ends. The open ends are formed on the holding side of the bodies of dipping pins. The body part and cap part are then cut to discard the uneven end, generally to industrial standard length. Body parts and cap parts are then fitted into a so-called pre-lock position and sold to customers who then fill the capsules with formulations. For the automated capsule dipping process, it is impossible to form closed container cavities on either cap part or body part because there will be no retrieving route for the dipping moulds. It is also impossible to form complex structures due to the fact the dipping pin bars can only dip one end into the capsule forming solution.

After a capsule is made from the automated dipping process, users of these pre-locked capsules will fill them in capsule filling machines. In a capsule filling machine, a capsule is opened to expose the open end of the body part and active formulations are filled into the capsule body cavity. The cap part is then telescopically pushed onto the body part and the capsules are locked using a "tongue and groove' mechanism to form one single cavity for holding pharmaceutical, nutritional or other therapeutic formulations (hereinafter referred to as "active formulations"). In this filling operation, cap parts of capsules are basically used as a closure and there is no attempt to fill the cap parts.

The walls of a capsule made from the aforementioned hard shell capsule automatic dipping process or soft gel die disc process are made of water soluble polymer(s) of natural, synthetic or semi-synthetic origin, such as, gelatin, pullulan, and hypromellose (HPMC). Capsule walls made by these processes always require uniformity in capsule constructive material because they form a single cavity for holding filling formulations. Therefore, all shell capsules made from a single molding process, either dipping for hard shell capsules or die disc molding of soft capsules currently in market can only sustain a single dissolution profile due to the uniformity in single constructive material.

However, the digestive track of mammalian digestion systems can differ dramatically from section to section in terms of pH, structure, pressure and functionalities. There are occasions that require a dual or multi dissolution profile for a plurality of combined active therapeutics. For example, a dual or multi dissolution profile is desirable to produce actives' synergy, stabilize the actives of therapeutics in stomach acid, enhance poor water-soluble actives, or moderate the concentration of actives in the blood between oral intake intervals. All these occasions demonstrate the necessity of being able to deliver actives in a different form and/or protected with an enteric coating. A single dissolution profile delivery vehicle becomes insufficient for these applications.

One of the solutions to having a plurality of active ingredients in one dosage delivery is by combining multiple active ingredients into one preparation. However, there are limitations to formulations containing multiple actives, such as solubility differences, absorption interferences, etc., that require further ingredients processing, such as granulation and film coating with various materials, in order to achieve reasonable effectiveness. The cost-effectiveness of formulations containing multiple actives reduces in direct proportion to increases in complexity of purposes, such as localizations, dosage frequency, and uniformity of drug delivery. Active therapeutic ingredient(s) that are poorly soluble, having high potency, having a short shelf life in stomach acid and that require large doses to be effective adds further complications for the single formulation solution.

Another solution available is using a capsule(s)-in-a-capsule or tablet(s)-in-a-capsule methodology (as described in U.S. Pat. No. 7,445,795). This methodology can provide two dissolution profiles, combining an immediate release dosage with a delayed release dosage to achieve sustained releasing phases. However, this technology does not demonstrate any advantages over taking multiple capsules and/or tablets in terms of costs and effectiveness because this technology requires multi-staged manufacturing. For example, capsule(s)-in-a-capsule manufacturing will require filling the smaller capsule(s) first, adding a coating if needed, then placing the smaller capsules inside a bigger capsule in a second stage that requires specialized equipment, and finally adding another coating if needed to achieve the two dissolution profiles.

Another solution is using a multi-compartment capsule technology. A considerable amount of research has been focused on the development of this technology for the delivery of a plurality of therapeutic and diagnostic agents in one dosage. The three current technologies being developed for compartmented hard capsules are: 1) adding an extra capsule cap or body onto a filled hard shell capsules (such as the Duo-Cap technology described in U.S. Pat. No. 9,456,990); 2) dividing the capsule body into two parts and filling the capsule from both ends (as described in WO 2019113653); and 3) adding dividing discs or barriers to the capsule cavity (as described in U.S. Pat. Nos. 7,670,612 and 8,361,497). However, these technologies can only achieve a single dissolution profile for immediate release without formulation enhancements such as micro-encapsulation and/or enteric coating. Furthermore, these technologies will either require multi-stage manufacturing using the current single dipping process, such as the aforementioned Duo-Cap technology, or it will be impossible to be manufactured by traditional dipping process due to its complexity (as described in WO2019113653 and U.S. Pat. No. 8,361,497). The multi-stage process and the more complex manufacturing process further inflates the costs of these technologies and reduces their cost-effectiveness, therefore limiting their practical mass industrial applications.

EP3,010,821 and EP2,575,788 disclosed fusing two soft capsules into one duo compartment soft shell capsules using soft gel technologies with die forming process, however, these teachings can not be referenced for manufacturing compartmented hard shell capsules because the totally different manufacturing process and purpose than multi-compartmented hard shell capsule (disc die cutting vs dip moulding).

A need exists to realign designs and manufacturing of compartmented capsules to eliminate the need for multi-stage manufacturing of the capsule itself in a traditional dip-molding process, and to streamline the complexity of the encapsulation process for encapsulating operations. Such realignment will increase cost-effectiveness of manufacturing compartmented capsules and its encapsulation process to a degree that its costs are comparable to or better than the sum of costs incurred for separately manufacturing each active ingredient into dosage form. Without such realignment, there is no desire in the industry to expand compartmented capsules' true usefulness for wider applications in pharmaceuticals, food products and diagnostic reagents.

A need exists for compartmented hard shell capsules that are capable of providing multiple dissolution profiles for active formulations, such as providing a combination of an immediate release dissolution profile for one active formulation and a delayed release profile for another active formulation all contained in the same compartmented hard shell capsule. Further need exist for a new compartmented capsule that match the functionalities offered by capsule-in-a-capsule or tablet-in-a-capsule technologies to include plurality of functions for active ingredient formulations, such as combination of targeting action site locations, protecting against active therapeutic degradation and reducing the blood concentration fluctuation between intakes of dosages.

SUMMARY

The present invention provides a compartmented hard shell capsule capable of having multiple dissolution profiles, such as providing a combination of an immediate release dissolution profile for one active formulation and a delayed release profile for another active formulation all contained in the same compartmented hard shell capsule.

The present invention provides a compartmented capsule that match the functionalities offered by capsule-in-a-capsule or tablet-in-a-capsule technologies to include plurality of functions for active ingredient formulations, such as combination of targeting action site locations, protecting against active therapeutic degradation and reducing the blood concentration fluctuation between intakes of dosages.

The compartmented hard shell capsule of the present invention can be formed, filled and encapsulated with modifications to the traditional forming, filling and encapsulation processes, eliminates the multi-stage manufacturing in current technologies, thereby increasing the cost-effectiveness for adoption and use of these compartmented hard shell capsule.

The compartmented hard shell capsule of the present invention is capable of providing combination of two dissolution profiles for active formulations, such as providing a combination of an immediate release dissolution profile for one active formulation and a delayed release profile for another active formulation all contained in the same compartmented hard shell capsule.

Through varying combinations of dissolution profiles of two compartments of present invention, the compartmented hard shell capsule can offer inclusion of function plurality for active ingredient formulations, such as combining of targeting action site locations with protecting against active therapeutic degradation or reducing the blood concentration fluctuation between intakes of dosages.

Accordingly, in one aspect, the disclosure provides a compartmented hard shell capsule for containing active formulations, and apparatuses and methods for forming, filling and encapsulating the compartmented hard shell capsules.

The compartmented hard shell capsule includes a cap portion having a hollow cavity defining a cap chamber and a body portion removably inserted into the cap portion. The body portion has an open end, a closed end and a sidewall defining a hollow cavity and a serrated edge along the open end, wherein the serrated edge may be folded over to form a barrier to enclose the body portion, thereby creating a body chamber that is separate from the cap chamber when the body portion is inserted into the cap portion.

In some embodiments, the compartmented hard shell capsule includes a serrated edge that is a plurality of triangle-shaped flaps 110 projecting from the open end. The plurality of triangle-shaped flaps 110 have overlapping edges when folded over to form the barrier.

In some embodiments, the compartmented hard shell capsule includes a serrated edge that is bent inwards towards the center of the body portion.

In some embodiments, the compartmented hard shell capsule includes a serrated edge that is bent inwards at an angle of about 1 to 10 degrees.

In some embodiments, the compartmented hard shell capsule includes a serrated edge that is bent inwards at an angle of about 2 to 3 degrees.

In some embodiments, the compartmented hard shell capsule includes a cap portion that is made of a different material composition from that of the body portion.

Apparatuses for forming a compartmented hard shell capsule includes dipping pin molds for forming a compartmented hard shell capsule. The dipping pin molds include a body pin bar and a cap pin bar. The body pin bar has a laterally extending body lock groove and a circumferential triangulated sloped portion located above the body lock groove. The cap pin bar has a laterally extending cap lock groove and a dimple indent located above the cap lock groove. The body pin bar forms a body portion of the compartmented hard shell capsule, the body lock groove forms a locking groove on the body portion, the circumferential triangulated sloped portion forms a serrated edge on the body portion, the cap pin bar forms a cap portion of the compartmented hard shell capsule, the cap lock groove forms a locking tongue on the cap portion, and the dimple indent forms a dimple on the cap portion.

In some embodiments, the dipping pin molds include a circumferential triangulated sloped portion that is an alternating series of raised triangles and recessed triangles. The raised triangles have a slope.

In some embodiments, the dipping pin molds include a slope that is about 1 to 5 degrees inward.

In some embodiments, the dipping pin molds include a slope that is about 2 to 3 degrees inward.

Methods of forming a compartmented hard shell capsule includes: dipping a cap pin bar and a body pin bar into a film forming solution; withdrawing the cap pin bar and the body pin bar from the film forming solution; allowing the film forming solution on the cap pin bar and body pin bar to dry to form a cap portion and a body portion of the compartmented hard shell capsule; removing the cap portion and body portion from the cap pin bar and body pin bar; and cutting the cap portion to the desired length. In this method, the body pin bar has a sloped triangulated portion comprising a plurality of alternating raised and recessed triangles and the force of removing body portion from the body pin bar will break the recessed triangles away from the body portion to form a serrated edge on the body portion.

Apparatuses for forming a chamber segment in a body portion of a compartmented hard shell capsule having a serrated edge includes a chamber formation segment, a sealing pin and a drying pin. The chamber formation segment includes a cavity to receive the body portion. The cavity includes an upper portion with an upper portion diameter, a bottom portion with a bottom portion diameter that is greater than the upper portion diameter, and a shoulder defined at an interface of the upper portion diameter and the bottom portion diameter, wherein the shoulder is operable to urge the serrated edge inwards and downwards. The sealing pin to apply a sealing solution to the serrated edge includes a hollow elongated body with a first end and a second end and a sintered porous tip at the second end, wherein the hollow elongated body contains a sealing solution for wetting the serrated edge, and the sealing solution is distributed through the sintered porous tip on to the serrated edge. The drying pin to dry the sealing solution on the serrated edge includes an elongated body with a first end and a second end and a flat tip at the second end, wherein the flat tip is used to apply heat to the serrated edge.

In some embodiments, the sealing solution has a preferred viscosity that allows the sealing solution to pass through the sintered tip but will not allow the sealing solution to freely drip from the sintered tip.

In some embodiments, the preferred viscosity is adjusted by varying the percentage of rheology modifiers in the sealing solution.

In some embodiments, the preferred viscosity is adjusted by modifying the pressure of the sealing solution.

Methods of forming a chamber segment in a body portion of a compartmented hard shell capsule having a serrated edge includes: folding down the serrated edge towards a center of the body portion; applying a sealing solution to the serrated edge; and drying the sealing solution on the serrated edge; wherein the application of the sealing solution and the drying of the sealing solution on the serrated edge seals the body portion and forms a barrier in the compartmented hard shell capsule.

Methods of forming a chamber segment in a body portion of a compartmented hard shell capsule having a serrated edge includes pushing the body portion into a bottom portion of a cavity of a chamber formation segment; inserting a sealing pin into an upper portion of the cavity to apply a sealing solution to the serrated edge; removing the sealing pin from the upper portion; and inserting a drying pin into the upper portion to dry the sealing solution on the serrated edge; wherein the application of the sealing solution and the drying of the sealing solution on the serrated edge seals the body portion and forms a barrier in the compartmented hard shell capsule.

In some embodiments, the methods of forming a chamber segment in a body portion of a compartmented hard shell capsule having a serrated edge further includes pushing the body portion against a shoulder in the cavity to push the serrated edge inwards and downwards.

In some embodiments, the drying pin dries the sealing solution by application of heat.

Embodiments can include combinations of the above features.

Further details of these and other aspects of the subject matter of this application will be apparent from the detailed description included below and the drawings.

DESCRIPTION OF THE DRAWINGS

Reference is now made to the accompanying drawings, in which.

DETAILED DESCRIPTION

The following disclosure relates to a compartmented hard shell capsule and apparatuses and methods for forming, filling and encapsulating compartmented hard shell capsules.

Aspects of various embodiments are described in relation to the figures.

Compartmented Hard Shell Capsule

Figure 1:
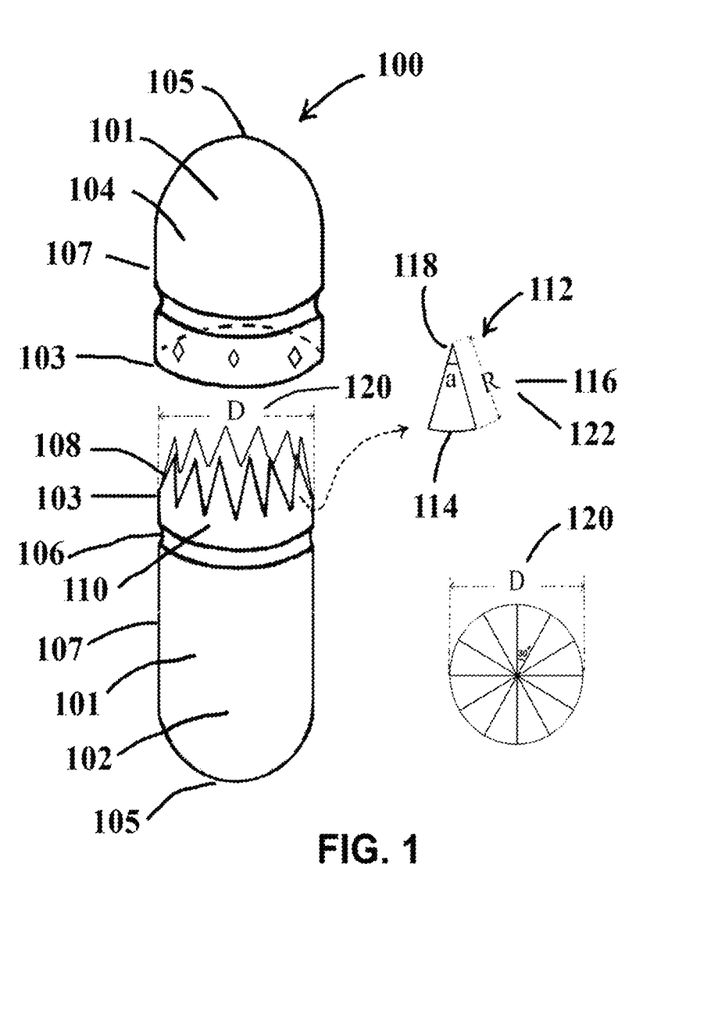
FIG. 1 is a front view of an embodiment of a compartmented hard shell capsule, showing the body portion separated from the cap portion.

FIG. 1 illustrates an embodiment of a compartmented hard shell capsule 100 (referred to hereinafter as CC capsule 100). CC capsule 100 includes a body portion 102 and a cap portion 104, each of which has a filling chamber 101. Both body portion 102 and cap portion 104 each has an open end 103, a closed end 105 and a sidewall 107 extending between open end 103 and closed end 105. Preferably, body portion 102 and cap portion 104 have approximately the same holding volume in terms of the volume of substance it can hold. The two filling chambers 101 will receive and hold different active formulations during the encapsulation process instead only the one chamber in traditional hard shell capsules. Therefore, compared to the traditional hard shell capsules, a shorter body and longer cap is more desirable in order to even the volume of filling chambers in terms of holding capacity or size. The holding volume of body of traditional hard shell capsules generally makes up around 80% total usable volume to fully utilize this sole receiving chamber during the encapsulation process. For example, traditional size #00 capsules have body chamber volume of about 0.71 ml, and cap chamber volume of about 0.24 ml. Accordingly, the most desirable split of body portion volume to cap portion volume would be close to 1:1, or about 0.475 ml each for size #00 capsules. CC capsule 100 can be designed to meet these requirements by adjusting the length of body portion 102 and cap portion 104.

Body portion 102 includes a groove 106 and a serrated edge 108. Serrated edge 108 is at the open end 103 of body portion 102. As illustrated in FIG. 1, serrated edge 108 is made up of a plurality of triangle-shaped flaps 110 in a cross-cut teeth pattern projecting from open end 103. However, it will be understood by a person skilled in the art that serrated edge 108 may be of variously shaped serrations, such as triangles in a rip teeth pattern.

Referring to FIG. 1, plurality of triangle-shaped flaps 110 include leaves 112, which are minor arc-shaped pieces. Leaves 112 have a base that is an arc 114, a side length 116 and a vertex angle 118. In order to balance the strength to remain upright during the process with the flexibility to be easily flattened down, the length of arc 114 is in the range of 0.5-3.5 mm and preferably in the range of 1.8-2.2 mm. Therefore, the circumferences of the opening end of body portion 102 determine the number of leaves 112 needed, that is, the diameter 120 of body portion 102 determines the number of leaves 112 on its edge. Diameter 120 of open end 103 of body portion 102 measured from the outside of body portion 102. For example, an industrial standard size #00 capsule body has a diameter of 8.18 mm and it is best to have 12 leaves, whereas a size #04 capsule body has a diameter of 5.06 mm and it is best to have 8 leaves. The side length 116 of leaves 112 equals to the radius 122 of open end 103 of body portion 102 measured on its outside in order to cover the whole open end 103 of body portion 102 after flattening down leaves 112. Vertex angle 118 is equal to 360 divided by the number of leaves 112 for plurality of triangle-shaped flaps 110. Preferably, each of leaves 112 have the same geometric measurements. Having the same geometric measurements facilitates simplicity and cost-effectiveness in the formation of CC capsule 100 during the automatic hard shell capsule dipping process.

As illustrated in FIG. 1, leaves 112 are slightly bent inward about 1-10 degrees and preferably about 2-3 degrees. During the encapsulation process, this slight bend of leaves 112 assists with the flattening of leaves 112 into a circle on the open end 103 of body portion 102, which later forms a barrier disc 113 that divides body portion 102 from cap portion 104 in a fully formed CC capsule 100. Beyond assisting in chamber formation in the encapsulation process, this slight bend of leaves 112 also facilitates the capsule formation process in the automatic dipping machine used in hard shell capsule manufacturing processes while avoiding interference with filling operations during the filling process.

Figure 2:
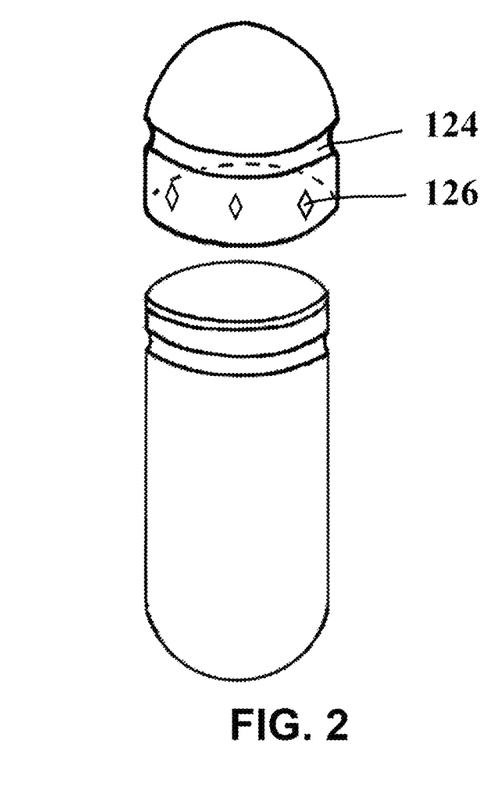
FIG. 2 is a front view of the embodiment of the compartmented hard shell capsule of FIG. 1, showing the leaves folded down.
Figures 3, 4:
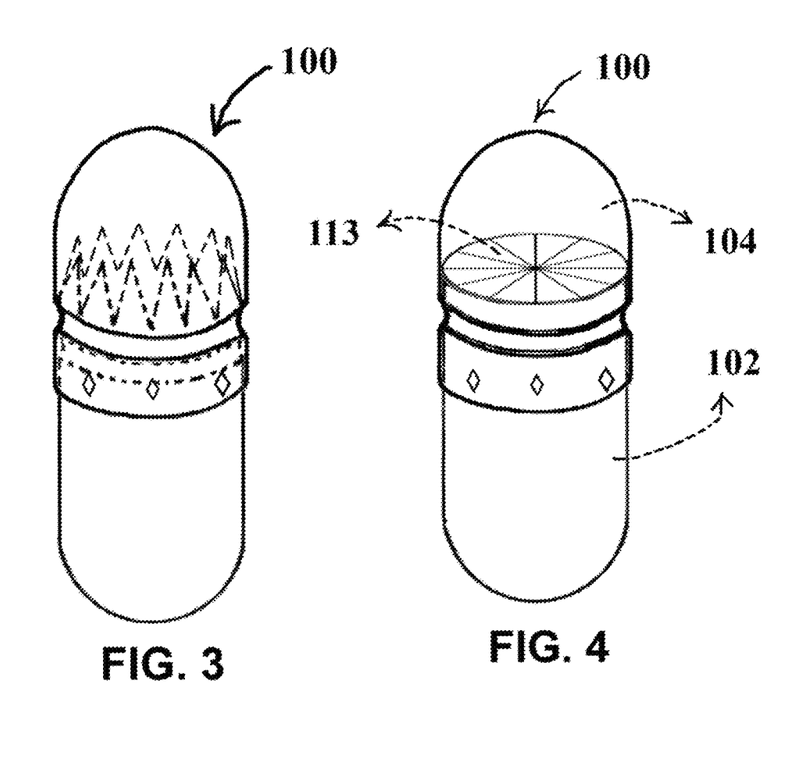
FIG. 3 is a front view of the embodiment of the compartmented hard shell capsule of FIG. 1, showing the body portion inserted into the cap portion in a pre-lock position.
FIG. 4 is a front view of the embodiment of the compartmented hard shell capsule of FIG. 1, showing the body portion inserted into the cap portion and the leaves folded down in a locked position.

Referring to FIG. 2, cap portion 104 includes a circumferential indentation or tongue 124 and dimples 126. Cap portion 104 fits over body portion 102. Tongue 124 is configured to engage groove 106 on body portion 102 to retain cap 104 onto body portion 102. Dimples 126 provide a pre-lock mechanism that removably holds cap portion 104 over body portion 102 prior to filling CC capsule 100 with active formulations. Once cap portion 104 and body portion 102 are filled with active formulations, tongue 124 is inserted into groove 106, cap portion 104 is locked into body portion 102. Accordingly, tongue 124 and groove 106 provides a locking mechanism for CC capsule 100.

Body portion 102 and cap portion 104 can each be formed of different materials in the same dip-molding process and thus allows for CC capsule 100 to have two different dissolution profiles, as long as body portion 102 is always the last filling chamber 101 to dissolve. The materials used to form CC capsule 100 can include a combination of film forming agents, solvents, rheology modifiers (with its cations initiator for some natural polysaccharides) and acid resistant film forming materials, if needed. Accordingly, CC capsule 100 can have any two combinations of the following release profiles: immediate mouth release, immediate stomach release, delayed stomach release, upper small intestine release, lower small intestine release, large intestine release and colon release. For example, body portion 102 can be made with enteric capsule ingredients (ingredients that do not dissolve in stomach acid), while cap portion 104 can be made with immediate release ingredients (ingredients that dissolve within 30 minutes), thus giving this CC capsule 100 guaranteed ability to deliver acid insensitive active ingredients into the stomach and acid sensitive ingredients directly into the small intestine. The two different dissolution profiles of CC capsule 100 can also be achieved by varying the proportions of capsule ingredients used to form each filling chamber 101. For example, some polysaccharide rheology modifiers and its initiating cations, such as alginates with calcium cations, can delay film dissolution of capsules that contain high concentrations of these polysaccharides.

Figure 5:
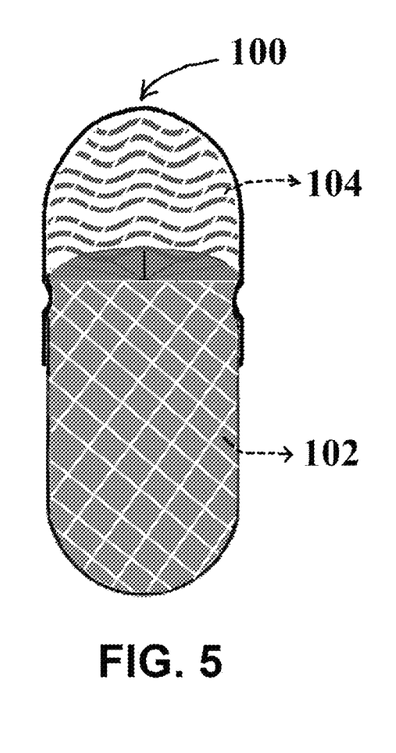
FIG. 5 is a cross-section view of the embodiment of the compartmented hard shell capsule of FIG. 4, showing the body portion holding a formulation and the cap portion holding a different formulation.

Body portion 102 and cap portion 104 can also be utilized to hold different forms of active formulations. As illustrated in FIG. 5, cap portion 104 is holding one active formulation and body portion 102 is holding a different active formulation. The different forms of active formulations can include, but is not limited to, any of the following forms: powder, granules, liquid, semi-liquid or paste. For example, body portion 102 can be used to encapsulate a liquid or semi-liquid formulation, and cap portion 104 can be used to encapsulate a powder formulation. This flexibility of having two filling chambers 101 each holding different forms of formulation could be combined with two different dissolution profiles to create a wide range of practical applications for delivering active pharmaceutical ingredients.

Apparatus and Method for Forming Compartmented Hard Shell Capsule

Figures 6, 7, 8:
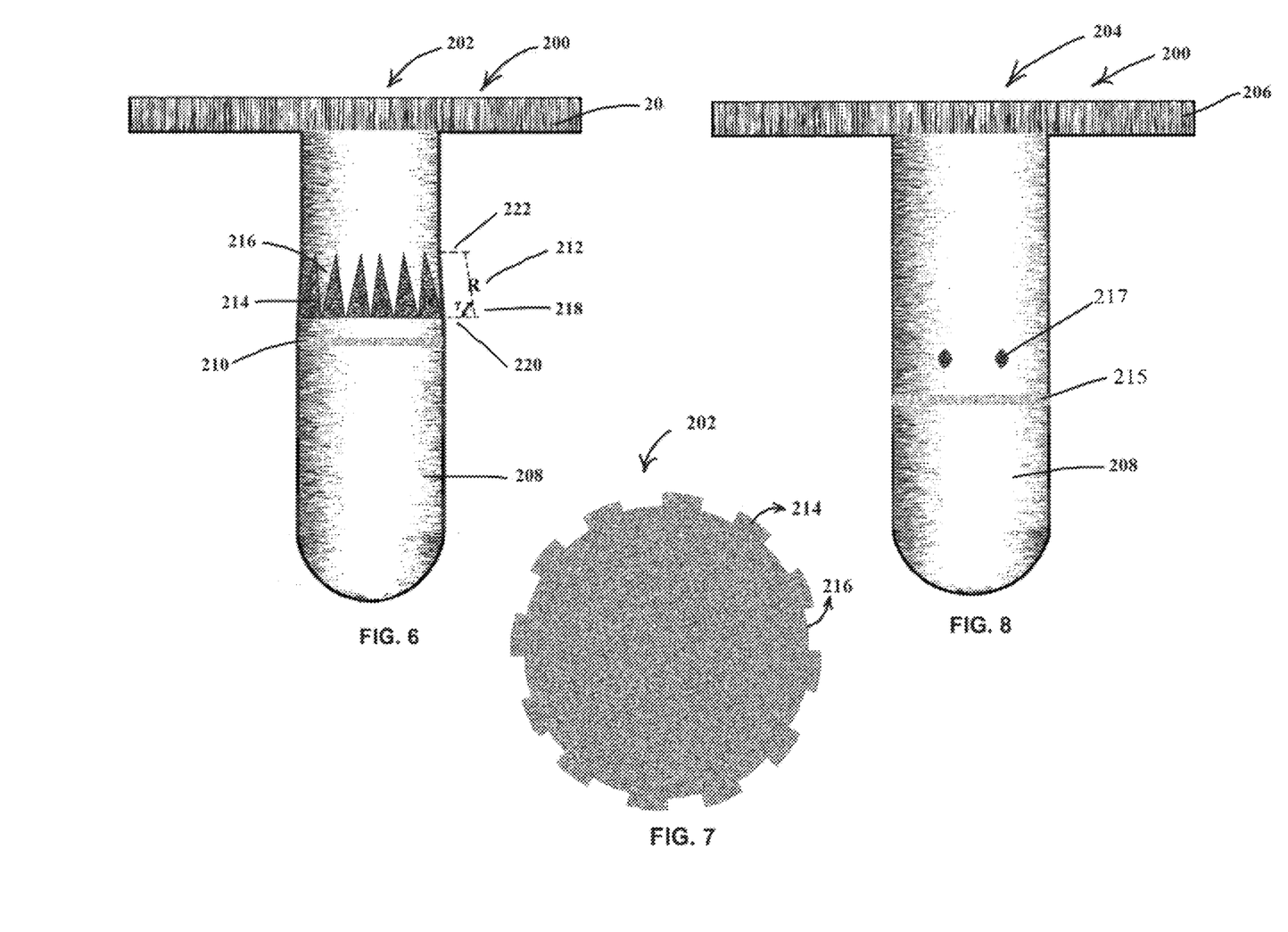
FIG. 6 is a front view of an embodiment of a body pin bar used to form the body portion of the compartmented hard shell capsule of FIG. 1.
FIG. 7 is a cross-section top view of the embodiment of the body pin bar of FIG. 6, showing a cross-section view at the middle of the sloped section.
FIG. 8 is a front view of an embodiment of a cap pin bar used to form the cap portion of the compartmented hard shell capsule of FIG. 1.

Referring to FIG. 6 and FIG. 8, specially shaped dipping pin bars 200 are used to form CC capsule 100. Dipping pin bars 200 include a body pin bar 202 and a cap pin bar 204. Both dipping pin bars 200 have a base 206 and a capsule-shaped mold 208.

Referring to FIG. 6, mold 208 on body pin bar 202 includes a body lock groove 210 and a circumferential triangulated sloped portion 212. Body lock groove 210 forms groove 106 on body portion 102 of CC capsule 100. Triangulated sloped portion 212 is located just above body lock groove 210. Triangulated sloped portion 212 is where leaves 112 of CC capsule 100 are formed. Triangulated sloped portion 212 includes raised triangles 214 and recessed triangles 216. Raised triangles 214 will form leaves 112 of CC capsule 100. The slope 218 of raised triangles 214 is about 1-5 degrees inward, and preferably 2-3 degrees inward. Slope 218 will make leaves 112 of CC capsule 100 naturally point inwards, but not inward enough to hinder the subsequent capsule filling process. The starting point 220 of slope 218 is located above body lock groove 210 and the stopping point 222 of slope 218 is determined by the radius 122 of CC capsule 100. Accordingly, the length of slope 218 equals the radius 122 of CC capsule 100. This ensures that when pushed down, the length of leaves 112 of CC capsule 100 will form a circular cover over the open end 103 of body portion 102.

Recessed triangles 216 will form the cut-off pieces of the plurality of triangle-shaped flaps 110 of CC capsule 100. Recessed triangles 216 are recessed inward by 80-130 microns, and preferably 95-105 microns from the inward slope 218 of raised triangles 214. This pattern of raised triangles 214 and recessed triangles 216 will reduce the complexity of cutting to form the serrated edge 108, or plurality of triangle-shaped flaps 110 of body portion 102 of CC capsule 100 in the conventional hard shell capsules' automatic hard shell dipping process. When removing the formed CC capsule 100 from body pin bar 202, the force of retrieving body pin bar 202 will break the recessed triangles 216 away from body portion 102.

Referring to FIG. 8, mold 208 on cap pin bar 204 includes a cap lock groove 215 and dimple indents 217. Cap lock groove 215 forms tongue 124 on cap portion 104 of CC capsule 100. Dimple indents 217 form dimples 126 on cap portion 104 of CC capsule 100.

Compared to the design of the conventional dipping pin bars for automatic hard shell capsule dip molding machines, the locking mechanism of dipping pin bars 200 are relocated by moving dimple indents 217 and cap lock groove 215 upward, so that the cap portion 104 of CC capsule 100 can be made a larger cap in comparison to conventional two-piece hard-shell capsules. Correspondingly, the body lock groove 210 of body pin bar 202 is moved downwards so that the body portion 102 of CC capsule 100 can be made smaller in comparison to conventional two-piece hard-shell capsules.

Dipping pin bars 200 are designed to replace the regular dipping pin bars of traditional automatic hard shell capsule dip molding machines. When an automatic dip molding machine is equipped with dipping pin bars 200, it can manufacture CC capsules 100 easily and continuously without other complicated modifications.

Using the automatic hard shell capsule dipping process to form CC capsules 100, dipping pin bars 200 are dipped into an aqueous-based film forming solution and subsequently withdrawn. The film formed on the surface of dipping pin bars 200 can then be dried, cut to a desired length and pattern and stripped off dipping pin bars 200, thereby obtaining body portion 102 and cap portion 104.

The film forming solution is any material that can be used as a base for forming any hard shell capsules. Examples include HPMC (e.g. HPMC types 2910, 2906 and/or 2208 as defined in USP30-NF25), gelatin, pullulan, PVA and non-enteric starch derivatives, such as hydroxypropyl starch or any combination thereof. The film forming solution can also include any acid resistant film forming agent. An acid resistant film forming agent is any material that can be used as an enteric coating agent for hard shell capsules. Examples include methacrylates copolymers, HPMC acetate succinate, HPMC phthalate, combination of polysaccharides, starch phthalate or combination thereof. The film forming solution can also include any number of pharmaceutically acceptable coloring agents, food acceptable coloring agents, or mixtures thereof. The coloring agents may be selected from azo-, quinophthalone-, triphenylmethane-, xanthene- or indigoid dyes, iron oxides or hydroxides, titanium dioxide, or natural dyes and mixtures thereof. Further examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, chlorophyllin, canthaxanthin, caramel, betanin and Candurin® pearlescent pigments. Candurin® is manufactured and marketed by Merck KGaA™, Darmstadt, Germany and consist of titanium dioxide and/or iron oxide-approved food and pharmaceutical colorants in many countries and potassium aluminum silicate as color carrier. In the film forming solution, pharmaceutically acceptable coloring agents, food acceptable coloring agents, or mixtures thereof are present in an amount ranging from about 0 to about 5 percent by weight, e.g., from about 0 to about 2.5 percent by weight, and from about 0 to about 1.5 percent by weight over the total weight of the aqueous composition.

Apparatus and Method for Filling and Encapsulation of Compartmented Hard Shell Capsule The process of filling body portion 102 and cap portion 104 of CC capsule 100 with active formulations and the process of closing off body portion 102 to form a compartment and locking cap portion 104 with body portion 102 (hereinafter referred to as the "filling process" and the "encapsulation process", respectively) in one continuous process can be achieved through modification of traditional encapsulation machines 600, such as the Bosch™ encapsulator, and use of specially designed chamber formation segments 300 that can be added to traditional encapsulation machines 600, along with a sealing pin 400 and a drying pin 500. The lower segments 604 of traditional encapsulation machines 600 are shortened and the upper segments 602 are lengthened to fit the length and contour of CC capsules 100. Chamber formation segments 300, sealing pin 400 and drying pin 500 assists with the formation of the barrier disc 113 that divides CC capsules 100 into two chambers during the encapsulation process.

Figure 9:
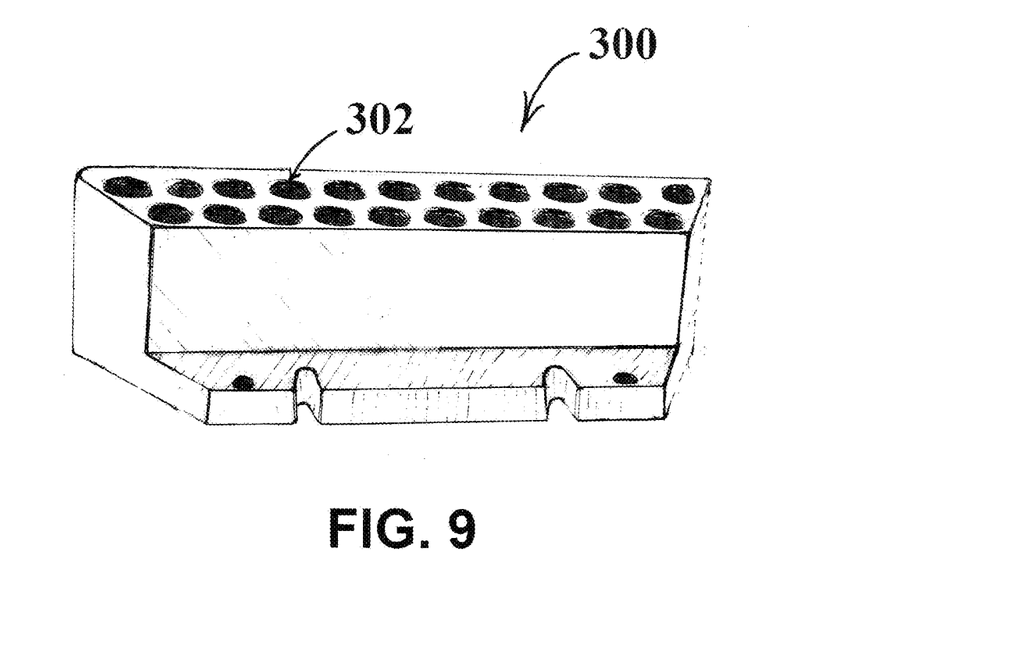
FIG. 9 is a perspective front view of a photo of an embodiment of a chamber formation segment used in the encapsulation process to form two separate filling chambers in the compartmented hard shell capsule of FIG. 4.
Figure 10:
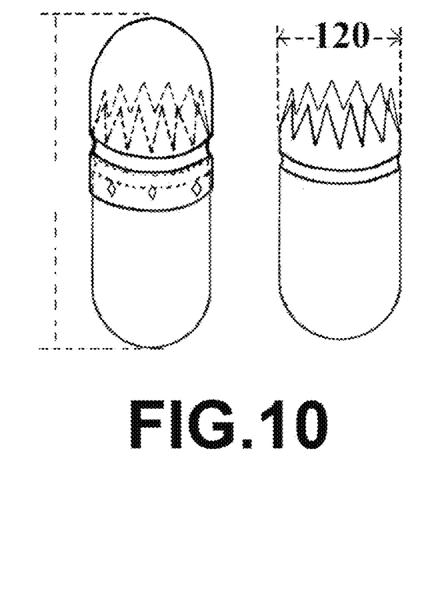
FIG. 10 is a illustration of the embodiment of the compartmented hard shell capsule of FIG. 1, showing the body portion inserted into the cap portion in a pre-lock position and the body portion by itself.
Figure 11:
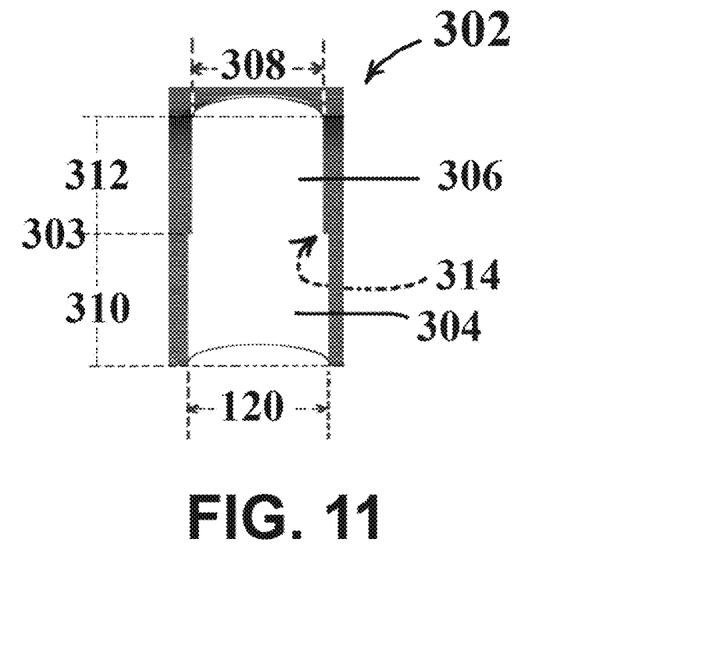
FIG. 11 is a perspective top cross-section view of a cavity in the embodiment of the chamber formation segment of FIG. 9.

Referring to FIG. 9, FIG. 10 and FIG. 11, chamber formation segment 300 have cavities 302 for securely holding body portion 102. The cavity length 303 of cavities 302 should be slightly longer than a pre-locked CC capsule 100 in order to hold body portion 102 and prevent the deformation of the shape and size of body portion 102 by sealing pin 400 and drying pin 500.

Cavities 302 have a bottom section 304 and an upper section 306. Bottom section 304 has the same diameter as diameter 120 of body portion 102. Upper section 306 has a smaller upper section diameter 308 that equals to diameter 120 of body portion 102 minus 1.5 to 4 times the thickness of sidewall 107 of body portion 102, and preferably two times the thickness of sidewall 107 of body portion 102. The thickness of sidewall 107 of traditional hard shell capsules is in the range of 90-110 microns and has an average of about 100 microns, or about 0.1 mm. Therefore, upper section diameter 308 of upper section 306 is about 0.2 mm smaller than the diameter of bottom section 304.

As illustrated in FIG. 11, the bottom section length 310 of bottom section 304 is approximately 0.4-0.65 of cavity length 303. The upper section length 312 of upper section 306 is approximately 0.35-0.6 of cavity length 303. Preferably, bottom section length 310 is 0.5-0.55 of cavity length 303 or equal to the midpoint of cavity 302. That is, preferably, bottom section length 310 is approximately equal to upper section length 312. Referring to FIG. 10 and FIG. 11, bottom section length 310 combined with upper section length 312 is equal to cavity length 303 and greater than the length of pre-locked CC capsule 100.

Referring to FIG. 11, a shoulder 314 is located at the point at which bottom section 304 meets with upper section 306. Shoulder 314 is formed from the difference in diameters between bottom section 304 and upper section 306. Accordingly, shoulder 314 is approximately 0.1-0.15 mm deep (when looking through bottom section 304). Shoulder 314 acts as a permanent structure to push leaves 112 of CC capsules 100 downward without making body portion 102 change in shape and size during the motion of pushing body portion 102 into cavity 302, as illustrated in FIG. 15.

Figure 12:
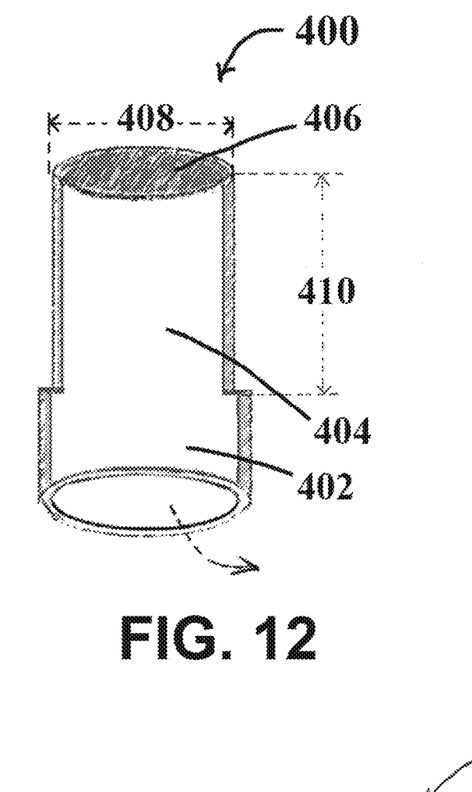
FIG. 12 is a perspective front view of an embodiment of a sealing pin used in the encapsulation process to form two separate filling chambers in the compartmented hard shell capsule of FIG. 4.
Figure 13:
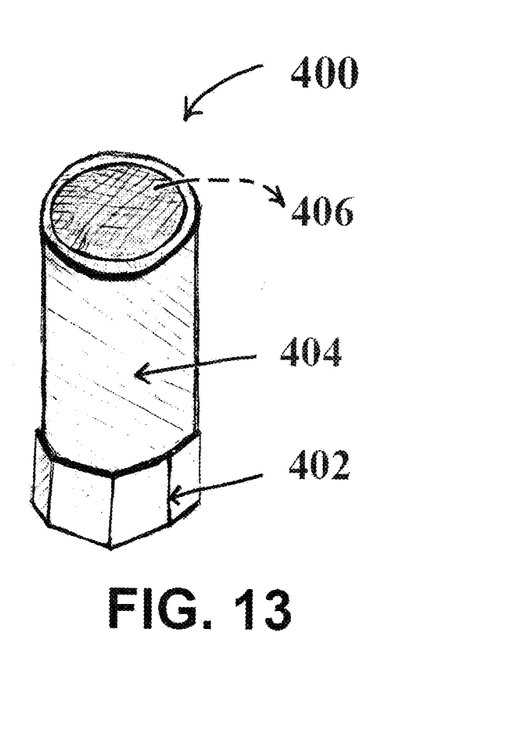
FIG. 13 is a photo of the perspective front view of the embodiment of the sealing pin of FIG. 12.
Figure 15:
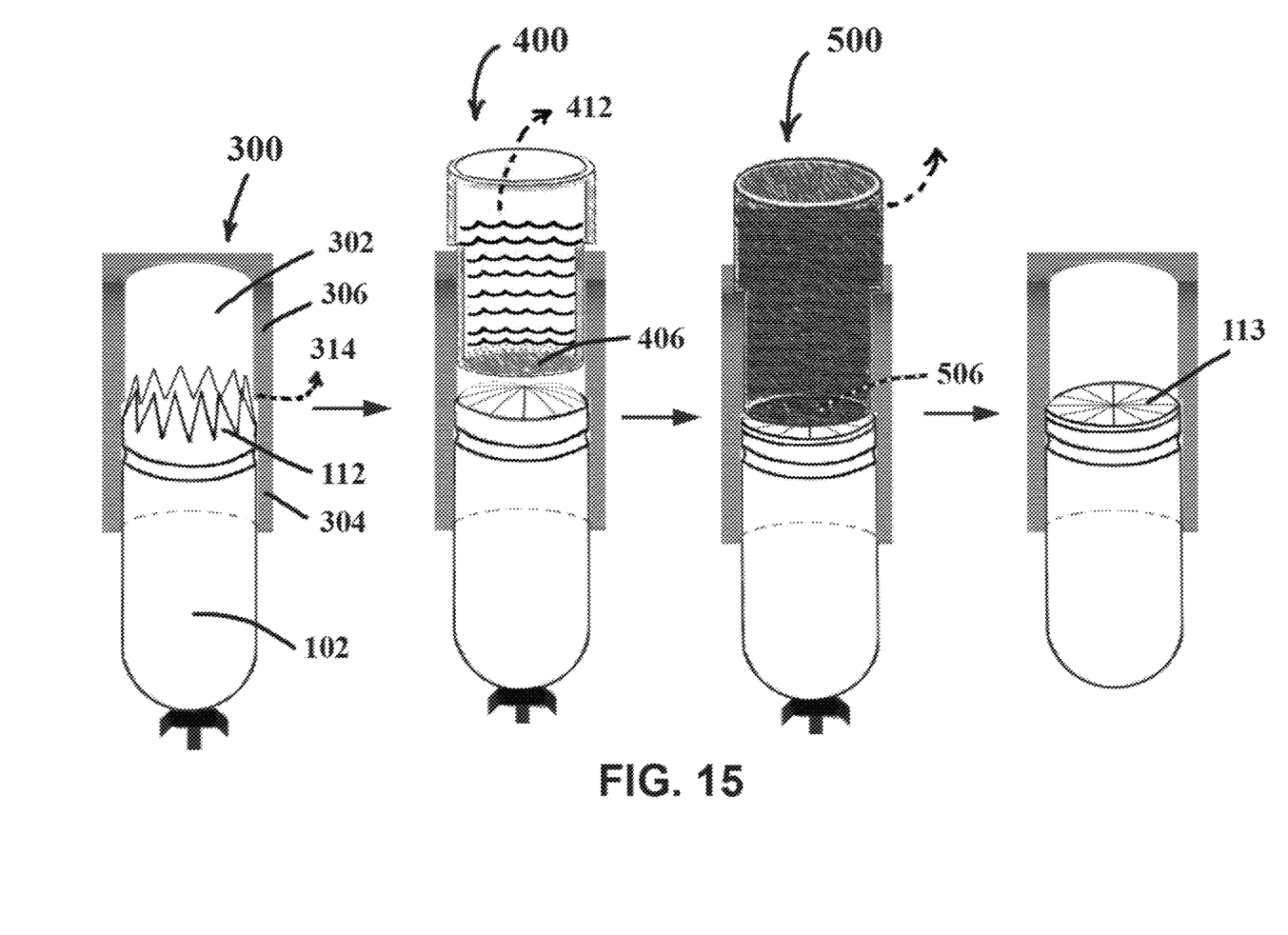
FIG. 15 is a perspective top cross-section view of the cavity in the embodiment of the chamber formation segment of FIG. 9, showing use of the embodiment of the sealing pin of FIG. 12, and the embodiment of the drying pin of FIG. 14 to form the two separate chambers in the compartmented hard shell capsule of FIG. 4.

Referring to FIG. 12, FIG. 13 and FIG. 15, sealing pin 400 includes a connector 402, a column 404 and a sintered porous tip 406. Connector 402 is a piece that can connect column 404 to a sealing solution reservoir, heating elements and/or a pressure modifying devices. Column 404 is a hollow cylindrical chamber connected to sintered porous tip 406. Column 404 has a column diameter 408 that is smaller than upper section diameter 308 of chamber formation segment 300. A column diameter 408 that is less than upper section diameter 308 accommodates for the varying temperatures that are maintained during the encapsulation process. Column 404 has a column length 410 that equals the upper section length 312 of chamber formation segment 300. Column 404 holds a volume of a sealing solution 412 that is to be applied to leaves 112 of CC capsule 100. Sintered porous tip 406 is a solid but porous tip that prevents sealing solution 412 from dripping from sealing pin 400 but remains consistently moistened. As illustrated in FIG. 13, sintered porous tip 406 is made of stainless steel and has a filtration size of between 0.1-20 microns and preferably between 1-2 microns. However, it will be understood by a person skilled in the art that sintered porous tip 406 could be made of other suitable materials and does not necessarily have to be made of sintered material.

Sealing solution 412 includes the same materials that are used to form CC capsule 100, with variation in the amount of the ingredients that can change the viscosity of sealing solution 412. Preferably, sealing solution 412 is similar to or the same in composition to the film forming solution used to form CC capsule 100 but adjusted to be made more viscous. Accordingly, sealing solution 412 may consist of a combination of film forming agents, solvents, rheology modifiers (with its cations initiator for some natural polysaccharides), and acid resistant film forming materials, if needed. For example, for gelatine CC capsules 100 that use both body portion 102 and cap portion 104 for immediate release, sealing solution 412 will only need gelatin (both acting as film forming agent and rheology modifier) and a solvent as ingredients. However, for gelatin CC capsules 100 that use body portion 102 as an enteric (acid resistant) chamber and cap portion 104 as an immediate release chamber, sealing solution 412 must contain gelatin, a solvent and the same enteric material used in the formation of body portion 102. Preferably, sealing solution 412 consists of: 1) at least one solvent such as water, lipophobic solvent or combinations thereof; 2) at least one film forming agent, such as gelatin, starch and its derivative, cellulose and its derivatives, pullulan and its derivatives, PVA, gums or combination thereof; 3) at least one rheology modifier such as cellulose derivatives, starch or derivatives, gums (such as guar gum, gum arabic, xanthan gum, alginates, carrageenan and gellen gum); 4) a wetting agent if needed; 5) a choice of plasticizers, coloring agent, release modifying agents, enteric coating material and surfactants that are deemed necessary to match the original composition of CC capsule 100; 6) a gliding agent if needed; and 7) an enteric material from one or combination of HPMC Acetate Succinate, HPMC Phthalate, Cellulose Acetate Phthalate, PVA Phthalate and methacrylates copolymer, if needed.

The viscosity of sealing solution 412 may be adjusted by varying the percentage of rheology modifiers in sealing solution 412. Rheology modifiers include but are not limited to alginates, agar gum, guar gum, locust bean gum, carrageenan, tara gum, gum arabic, ghatti gum, Khaya grandifolia gum, tragacanth gum, karaya gum, pectin, arabian (araban), xanthan, gellen, starch, Konjac mannan, galactomannan, funoran, and other exocellular polysaccharides. Preferably, the viscosity of sealing solution 412 is adjusted such that sealing solution 412 can pass through and will always wet the contacting surface of sintered porous tip 406 but not be freely dripping from sintered porous tip 406 due to gravity. The temperature of sealing solution 412 is kept consistently above the melting temperature of sealing solution 412 with a heating device connected to sealing pin 400. Accordingly, the viscosity of sealing solution 412 is the viscosity measured at its melting point temperature.

In an alternative embodiment, sealing pin 400 is connected through tubes to a pressure regulating device that modifies the pressure of sealing solution 412 to achieve the same result as adjusting the percentage of rheology modifiers to change the viscosity of sealing solution 412.

Figure 14:
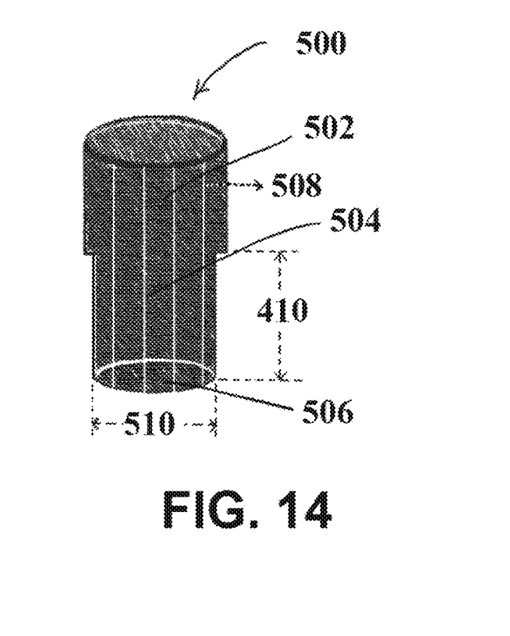
FIG. 14 is a perspective front view of an embodiment of a drying pin used in the encapsulation process to form two separate filling chambers in the compartmented hard shell capsule of FIG. 4.

Referring to FIG. 14 and FIG. 15, drying pin 500 includes a connector 502, a column 504 and a flat tip 506. Connector 502 is connected to heating elements and a temperature sensor to keep column 504 heated to a temperature range suitable for quick drying of sealing solution 412. Column 504 is a solid cylindrical mass connected to flat tip 506. As illustrated, column 504 is made of solid stainless steel. However, it will be understood by a person skilled in the art that column 504 may be made of any other suitable material. Column 504 has vapor channels 508 located all along its sides. Vapor channels 508 are longitudinal vapor vent depressions in column 504 that allow for any moisture produced from the of heating sealing solution 412 to escape from upper section 306 of cavity 302. Column 504 has the same length as the column length 410 of sealing pin 400. However, column 504 has a column diameter 510 is smaller than column diameter 408 of sealing pin 400. For example, column diameter 510 of drying pin 500 may be smaller than column diameter 408 of sealing pin 400 by the thickness of sidewall 107 of CC capsule 100. This smaller column diameter 510 ensures that drying pin 500 can be inserted into cavity 302 of chamber formation segment 300 when the heat applied to drying pin 500 expands the size of drying pin 500.

Drying pin 500 is heated to a temperature best suited for drying ingredients used to form body portion 102 and sealing solution 412 and to allow sealing solution 412 to permanently bind on leaves 112 and to form an intact barrier disc 113. The temperature of drying pin 500 may vary in the range of 36-65 degrees Celsius depending on the melting point temperature of the ingredients used to form body portion 102. For example, the best temperature to be used for drying pin 500 to melt and dry a gelatin body portion 102 is around 42-45 degrees Celsius, which is 7-10 degrees Celsius above gelatin's 35 degrees Celsius melting point temperature. For pullulan capsules that lack thermo-reverse ability, the temperature to be used for drying pin 500 may be set to around 55 degrees Celsius to achieve the goal of quick drying body portion 102. Ultimately, in order to achieve the best results, the most desirable temperature to be used for drying pin 500 is to be determined on a case by case basis by the operator and is based on the melting point of the particular ingredients used to form body portion 102.

Figure 16:
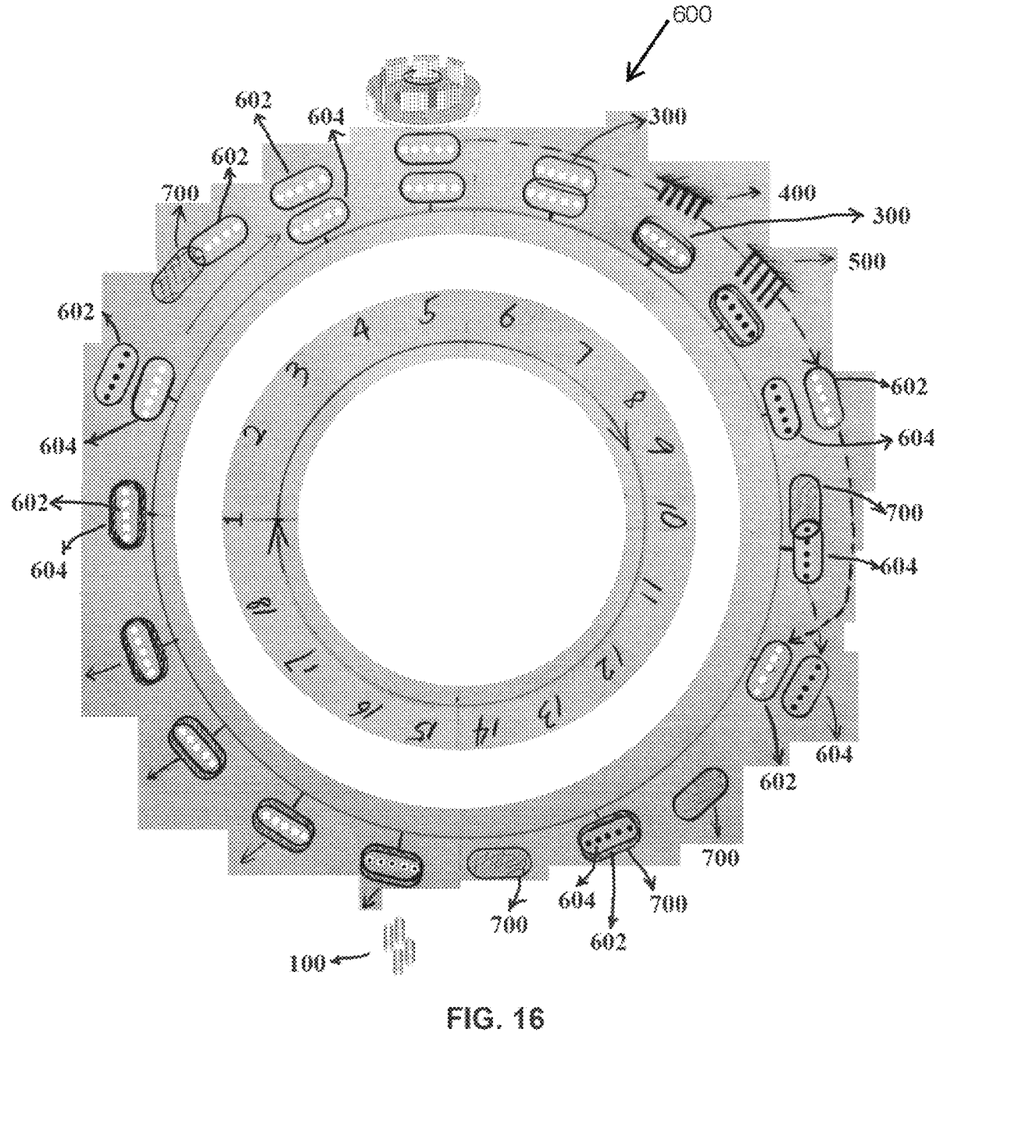
FIG. 16 is a process diagram showing the one continuous encapsulation flow design, in which forming the two separate chambers in the compartmented hard shell capsule of FIG. 4, using the embodiment of the chamber formation segment of FIG. 9, the embodiment of the sealing pin of FIG. 12, and the embodiment of the drying pin of FIG. 14 are all incorporated in one circular process.

Referring to all the figures generally, but to FIG. 16 particularly, in operation, CC capsules 100 are placed in a traditional encapsulation machine 600 with the modifications as previously described (i.e., chamber formation segments 300, sealing pin 400 and drying pin 500 are installed). CC capsules 100 are then sequenced and opened by vacuum as per the traditional encapsulation process. After opening of the CC capsules 100, an upper segment 602 holding cap portions 104 is turned by 180 degrees laterally with a flat assist plate 700 attached to it to prevent cap portions 104 from falling off by gravity. This 180 degree flip exposes open end 103 of cap portions 104 for filling with chemical formulations. A lower segment 604 holds body portions 102 for filling with chemical formulations. Both body portions 102 and cap portions 104 are then filled with the desired active formulations. After both body portions 102 and cap portions 104 are filled, body portions 102 are pushed from lower segment 604 with a pushing pin into the stationary chamber formation segment 300 when the holes of lower segment 604 align with cavities 302 of chamber formation segment 300. Then, in the chamber formation segment 300, leaves 112 of CC capsules 100 are pushed down, wet with sealing solution 412 and dried by drying pin 500.

Referring to FIG. 15, in chamber formation segment 300, body portions 102 are pushed into cavities 302 through the larger bottom section 304. When leaves 112 of body portions 102 arrive at shoulder 314, shoulder 314 will exert downward pressure on leaves 112 towards the center of body portion 102. When body portion 102 is fully inserted into chamber formation segment 300, leaves 112 of body portion 102 are all pushed down towards the center of body portion 102. Once all the leaves 112 have been pushed down, sealing pin 400 is inserted into upper section 306 of chamber formation segment 300. A suitable amount of sealing solution 412 is applied through the sintered porous tip 406 of sealing pin 400 to wet the pushed down leaves 112. Sealing pin 400 is then removed from upper section 306 and drying pin 500 is inserted into upper section 306. Heat is applied to the pushed down leaves 112 through drying pin 500. Heat applied through drying pin 500 will dry and firm the now formed barrier disc 113. For CC capsules 100 with an enteric material coated on to its body portion 102 that is not water soluble, optionally, the sealing process of leaves 112 can be divided into two steps: 1) sealing pin 400 spreads a water-based sealing solution 412 on to leaves 112, then drying pin 500 dries the sealing solution 412 on leaves 112; and 2) a second sealing pin 400 spreads a solvent-based enteric coating sealing solution 412 onto disc 113, then drying pin 500 dries the sealing solution 412 again to form the enteric coating layer. Pushing pins are then retrieved from lower segment 604 and body portion 102 falls back into lower segment 604 from chamber formation segment 300 due to gravity.

Referring to FIG. 16, after leaves 112 of CC capsules 100 have formed barrier disc 113, lower segment 604 is turned 180 degrees laterally with another flat assist plate 700. When upper segment 602 and lower segment 604 align, the flat assist plate 700 for lower segment 604 is removed and body portion 102 is pushed into the filled cap portion 104 and into a locked position. CC capsules 100 are then fully filled. The flat assist plate 700 for upper segment 602 is then removed and the filled CC capsules 100 will drop out of the holes of upper segment 602 due to gravity because both upper segment 602 and lower segment 604 were turned 180 degrees laterally in the process. Both upper segment 602 and lower segment 604 are then returned to their original positions by turning both segments 180 degree laterally. The holes of both upper segment 602 and lower segment 604 are cleaned with air and returned to their starting position, ready to accept the next round of empty CC capsules 100.

An example of the filling and encapsulation process for CC capsule 100 using a modified automatic filling and encapsulation machine is illustrated in FIG. 16. The following is a description of steps 1 to 18 in the turning table process of the modified automatic filling and encapsulation machine. The numbers in the inner ring of FIG. 16 represent the step numbers. In step 1, CC capsules 100 are dropped into segments where upper segment 602 and lower segment 604 are aligned for taking pre-locked capsules, same as in traditional encapsulation machine 600 from a sequence magazine. At step 2, using a vacuum force, CC capsules 100 are opened and separated into its body portion 102 and cap portion 104. Lower segment 604 holds body portion 102 with its open end 103 facing upwards. Upper segment 602 holds cap portion 104 with its closed end 105 facing upwards. In step 3, flat assist plate 700 is used to hold cap portions 104 within upper segment 602 as upper segment 602 is turned 180 degrees. At step 4, upper segment 602 has been turned 180 degrees such that open end 103 of cap portion 104 is now facing upwards. In step 5, a dosing operation fills body portions 102 and cap portions 104 with active formulations. At step 6, body portions 102 in lower segment 604 are pushed up into the bottom section 304 of stationary chamber formation segment 300. As body portions 102 are pushed into cavities 302, leaves 112 are pushed against shoulder 314, which forces leaves 112 inwards and downwards. In step 7, sealing pins 400 are inserted into upper section 306 of chamber formation segment 300 to spread sealing solution 412 onto leaves 112. Once sealing solution 412 has been applied, sealing pins 400 are withdrawn from upper section 306. In step 8, drying pins 500 are inserted into upper section 306 to dry sealing solution 412 on leaves 112. Once sealing solution 412 is dried, leaves 112 form barrier disc 113, which closes body portion 102. Drying pins 500 are then withdrawn. At step 9, upper segment 602, which had bypassed steps 6 to 8, align back up with lower segment 604, which now contains filled and closed body portions 102. In step 10, flat assist plate 700 is used to hold body portions 102 within lower segment 604 as lower segment 604 is turned 180 degrees. At step 11, upper segment 602 containing filled cap portions 104 with its open ends 103 facing upwards are located at the bottom, and lower segment 604 containing filled and closed body portions 102 is located at the top. Due to both upper segment 602 and lower segment 604 having been turned 180 degrees, upper segment 602 and lower segment 604 have effectively swapped positions in relation to their original positions in step 2. In step 12, flat assist plate 700 on lower segment 604 is removed and closed body positions 102 drop from lower segment 604 into cap portions 104 in upper segment 602 to form filled pre-locked CC capsules 100. At step 13, filled pre-locked CC capsules 100 are pushed from the top to snap close CC capsules 100 into its locked position. In step 14, flat assist plate 700 is removed from upper segment 602. At step 15, filled pre-locked CC capsules 100 drop out from upper segment 602 due to gravity. At step 16, both upper segment 602 and lower segment 604 are turned 180 degrees to return to their original positions in step 2. In step 17, both upper segment 602 and lower segment 604 are cleaned with compressed air. At step 18, an automatic alignment check is conducted. Accordingly, the filling process and encapsulation process of CC capsules 100 occur in one continuous operation.

EXAMPLES

The following are some non-limiting examples of possible implementations of the present technology.

An experimental manual capsule dipping machine is modified to manufacture CC capsules 100 with dipping pin bars 200 and modified cutting tools that allows lateral and circular cutting after CC capsules 100 are dried.

A NJP-1200 encapsulation machine that is capable of running at 70,000 capsules per hour is modified for present embodiment. The turning table of the machine is enlarged to accommodate more stations. An auxiliary motor and auxiliary mechanical design are added to perform turning of segments with the assistance of flat assist plates. A double line dosing is installed on the NJP-1200 instead of the regular one line dosing. CC capsule 100 forming segments are installed on the machine instead of regular capsule segments. The sealing pin 400 and drying pin 500 are stationed next to the dosing device and heating is achieved by placing the sealing pin 400 inside electrically heated holster that is isolated from the NJP-1200 machine to prevent transfer of heat to the filling machine.

Testing method of success rate: there is no widely accepted or even known method to test how successful duo compartment/compartmented capsules are. Due to the fact that the entire purpose of compartmented capsules is to separate the filling materials of compartments, therefore, the key indicator in any design of compartmented capsules should be no leakage between the compartments. Accordingly, a modified method for testing for capsule leakages is needed. Liquid is generally the best testing material for testing capsule leakage due to the fact that capsules are used for the human digestion tract, which is filled with semi-liquid. Therefore, a solvent that does not dissolve the capsule structure is the best material that can be used for testing.

Gelatin, hypromellose and pullulan are all insoluble in pure ethanol and vegetable oils. Pure canola oil is chosen as the liquid of choice in our experiments here because it is less viscous and also not volatile.

Cut the closed end 105 of body portion 102 of a filled CC capsule 100 with brown and white rice and pour out the filling contained in body portion 102. Then set the filled CC capsule 100 vertical with cut out part on top. Fill the remaining body portion 102 with pure canola oil and observe for leakage after 60 minutes. If there is no oil appearing at the opposite side of barrier disc 113, then it records as a success, otherwise it records as a failure.

Example 1

Manufacturing CC capsule 100: size #00 body pin bar 202 and cap pin bar 204 are dipped into capsule forming gelatin solution made of 23% gelatin, 0.1% glycerin and 76.9% water. After air tunnel drying to achieve a moisture level of 15-17%, capsule is cut to size and pre-locked similar to regular gelatin capsules for use.

A modified NJP-1200 encapsulation machine with all the modifications running less than half of its maximum speed of 72,000 capsules per hour is used. The temperature of sealing pin 400 is heated to 38-40 degrees Celsius, sealing solution comprise of 26% gelatin, 0.1% glycerin and 73.9% water. The temperature of drying pin 500 is set to 48-50 degrees Celsius. Filling material for body portion 102 of CC capsule 100 is brown rice powder, and filling material cap portion 104 of CC capsule 100 is white rice powder.

After filling, cut the closed end 105 of body portion 102 and drain the brown rice powder, inject canola oil into body portion 102 and set the CC capsule 100 upright for 1 hour to check for leaks. 3 filled CC capsule 100 were subjected to USP <701> basket disintegration testing method in pH 6.8 buffer solution. Results are shown below.

| No. of Leaves/capsule | 8 pieces | 12 pieces | 16 pieces |
|---|---|---|---|
| Running Speed | 20,000 per hour | 20,000 per hour | 20,000 per hour |
| Moisture of CC capsule | 16.5% | 16.5% | 16.5% |
| Success rate | 91.4% | 99.1% | 95.3% |
| Disintegration time (minutes) | 7 | 9 | 8 |

The number of leaves 112 on body portion 102 of CC capsule 100 works the best around 12 pieces. Too many leaves 112 results in small chips and breaks of the leaves 112 due to their small size. However, 8 large pieces resulted in increased leaking around the connection area between two leaves 112 and sidewall 100.

The disintegration time of the CC capsule 100 where the seal is good and intact is almost the same as normal gelatin capsules of the same composition. The weak spots created by leaves 112 that are too large or too small reduced the integrity of the sealed CC capsule 100 and therefore, reduced the disintegration time of those CC capsules 100.

Example 2

Manufacturing CC capsules 100: heated size #00 body pin bar 202 and cap pin bar 204 are dipped into cold capsule forming hypromellose solution made of 25% hypromellose and 75% water. After air tunnel drying to achieve a moisture level of 5-7%, CC capsules 100 are cut to size and pre-locked similar to regular hypromellose capsules for use.

A modified NJP-1200 encapsulation machine with all the modifications running less than half of its maximum speed of 72,000 capsules per hour is used. The temperature of drying pin 500 is set to 43-48 degrees Celsius and the temperature of sealing pin 400 is at room temperature, sealing solution 412 is made of 26% hypromellose, 0.1% xanthan gum and 73.9% water. Filling material for body portion 102 of CC capsule 100 is brown rice powder, and filling material for cap portion 104 of CC capsule 100 is white rice powder.

After filling, cut the closed end 105 of body portion 102 and drain the brown rice powder, inject canola oil into body portion 102 and set the capsule upright for 1 hour and check for leaks. 3 filled CC capsules 100 are subjected to USP <701> basket disintegration testing method in pH 6.8 buffer solution. Results are shown below.

| No. of Leaves/capsule | 8 pieces | 12 pieces | 16 pieces |
|---|---|---|---|
| Running Speed | 20,000 per hour | 20,000 per hour | 20,000 per hour |
| Moisture of CC capsule | 5.6% | 5.6% | 5.6% |
| Success rate | 96.1% | 99.7% | 97.6% |
| Disintegration time (minutes) | 5 | 6 | 6 |

The number of leaves 112 on CC capsules 100 works the best around 12 pieces. Although too many leaves 112 still result in small chips and breaks due to the small size, the number of breakages is remarkably reduced in comparison to gelatin CC capsules 100. Same can be said about 8 large pieces of leaves 112, it still results in increased leaking around the connection area of two leaves 112 and sidewall 107, but significantly less when compared to gelatin CC capsules 100. The results reflect the fact that hypromellose CC capsules 100 are much more flexible and less rigid than the gelatin CC capsules 100.

The disintegration time of hypromellose CC capsules 100 where the sealing is good and intact is almost the same as normal hypromellose capsules of the same composition. When there is a weak spot created by leaves 112 that are too large or too small the integrity of the CC capsule 100 is reduced therefore, reducing the disintegration time of that CC capsule 100.

Example 3

Manufacturing CC capsules: size #00 body pin bar 202 and cap pin bar 204 are dipped into a capsule forming pullulan solution made of 23% pullulan, 0.2% alginate potassium salt, 0.1% glycerin and 76.7% water. After applying de-humidified air tunnel drying to achieve moisture level of 12-14%, CC capsules 100 are cut to size and pre-locked similar to regular pullulan capsules for use.

A modified NJP-1200 encapsulation machine with all the modifications running less than half of its maximum speed of 72,000 capsules per hour is used. The temperature of sealing pin 400 is set to 38-40 degrees Celsius and drying pin 500 is heated to 48-50 degree Celsius. Sealing solution 412 is made of 27% pullulan, 0.3% alginate potassium salt, 0.1% glycerin and 72.6% water. Filling material for body portion 102 is brown rice powder, and filling material for cap portion 104 is white rice powder.

After filling, cut the closed end 105 of body portion 102 and drain the brown rice powder, inject canola oil into body portion 102 and set the capsule upright for 1 hour to check for leaks. 3 filled CC capsule 100 are subjected to USP <701> basket disintegration testing method in pH 6.8 buffer solution. Results are shown below.

| No. of Leaves/capsule | 8 pieces | 12 pieces | 16 pieces |
|---|---|---|---|
| Running Speed | 20,000 per hour | 20,000 per hour | 20,000 per hour |
| Moisture of CC capsule | 12.9% | 12.9% | 12.9% |
| Success rate | 94.3% | 99.2% | 96.3% |
| Disintegration time (minutes) | 4 | 6 | 6 |

The number of leaves 112 on CC capsule 100 works the best around 12 pieces. Pullulan capsules are very similar to gelatin capsules in terms of the rigidity of sidewall 107 and leaves 112. Too many leaves 112 still result in small chips and breaks due to their small size. Leaves 112 that are too large result in increased leaking around the connection area of two leaves 112 and sidewall 107.

The disintegration time of the pullulan CC capsule 100 is almost the same as the disintegration time of normal pullulan capsules of the same composition when the sealing is good and intact. When there is a weak spot created by leaves 112 that are too large or too small the integrity of the pullulan CC capsule 100 is reduced therefore, reducing the disintegration time of that pullulan CC capsule 100.

Example 4

Manufacturing CC capsules: size #00 body pin bar 202 and cap pin bar 204 are dipped into a capsule forming gelatin solution made of 23% gelatin, 0.1% glycerin and 76.9% water. After air tunnel drying to achieve a moisture level of 15-17%, CC capsules 100 are cut to size and pre-locked similar to regular gelatin capsules for use.

A modified NJP-1200 encapsulation machine with all the modifications running half of its maximum speed of 72,000 capsules per hour is used. The temperature of sealing pin 400 is set to 38-40 degrees Celsius, sealing solution is made of 26% gelatin, 0.1% glycerin and 73.9% water. The temperature of drying pin 500 is set to 48-50 degree Celsius. Filling material for body portion 102 is brown rice powder, and filling material for cap portion 104 is white rice powder.

After filling, cut the closed end 105 of body portion 102 and drain the brown rice powder. Inject canola oil into body portion 102 and set the CC capsule 100 upright for 1 hour to check for leaks. Results are shown below.

| No. of Leaves/capsule | 8 pieces | 12 pieces | 16 pieces |
|---|---|---|---|
| Running Speed | 36,000 per hour | 36,000 per hour | 36,000 per hour |
| Moisture of CC capsule | 16.5% | 16.5% | 16.5% |
| Success rate | 90.2% | 99.4% | 92.9% |

The number of leaves 112 on the CC capsules 100 works the best around 12 pieces. The increased speed did not change the outcome.

Example 5

Manufacturing CC capsules 100: heated size #00 body pin bar 202 and cap pin bar 204 are dipped into cold capsule forming hypromellose solution made of 25% hypromellose and 75% water. After air tunnel drying to achieve moisture level of 5-7%, CC capsules 100 are cut to size and pre-locked similar to regular hypromellose capsules for use.

A modified NJP-1200 encapsulation machine with all the modifications running at normal recommended speed of its maximum speed of 72,000 capsules per hour is used. The temperature of drying pin 500 is set to 43-48 degrees Celsius, sealing pin 400 is running at room temperature, sealing solution 412 is made of 26% hypromellose, 0.1% xanthan gum and 73.9% water. Filling material for body portion is brown rice powder, and filling material for cap portion is white rice powder.

After filling, cut closed end 105 of body portion 102 and drain the brown rice powder, inject canola oil into body portion 102 and set the CC capsule 100 upright for 1 hour to check for leaks. Results are shown below.

| No. of Leaves/capsule | 8 pieces | 12 pieces | 16 pieces |
|---|---|---|---|
| Running Speed | 60,000 per hour | 60,000 per hour | 60,000 per hour |
| Moisture of CC capsule | 5.6% | 5.6% | 5.6% |
| Success rate | 93.8% | 99.8% | 95.2% |

The folding and sealing of leaves 112 on the CC capsules 100 work the best around 12 pieces even at regular running speed, similar to the finding of process running at much slower speed.

Example 6

Manufacturing CC capsules: heated size #00 CC body pin bar 202 is dipped into a cold capsule forming solution made of 20% hypromellose, 7% water soluble hypromellose acetate succinate and 73% water, and cap pin bar 204 is dipped into hypromellose solution comprise of 25% hypromellose and 75% water. After air tunnel drying to achieve a moisture level of 5-7%, CC capsules 100 are cut to size and pre-locked similar to regular hypromellose capsules for use.

A modified NJP-1200 encapsulation machine with all the modifications running at normal recommended speed of its maximum speed of 72,000 capsules per hour is used. The temperature of drying pin 500 is set to 43-48 degrees Celsius. Sealing pin 400 is operating at room temperature, sealing solution is made of 22% hypromellose, 7% of water soluble hypromellose acetate succinate, 0.1% xanthan gum and 70.9% water. Filling material for body portion 102 is brown rice powder, and filling material for portion 104 is white rice powder.

After filling, cut the closed end 105 of body portion 102 and drain the brown rice powder, inject canola oil into body portion 102 and set the CC capsule 100 upright for 1 hour to check for leaks. Besides normal disintegration of the whole filled CC capsule 100, 3 body portions 102 of filled CC capsules 100 are subjected to USP <701> basket dissolution testing method in simulated gastric fluid (SGF) with pH set to 1.0. Results are shown below.

| No. of Leaves/capsule | 8 pieces | 12 pieces | 16 pieces |
|---|---|---|---|
| Running Speed | 60,000 per hour | 60,000 per hour | 60,000 per hour |
| Moisture of CC capsule | 5.7% | 5.7% | 5.7% |
| Success rate | 88.6% | 98.8% | 93.1% |
| Cap cavity disintegration minutes | 4 | 6 | 5 |
| Body cavity intact in USP simulated gastric fluid pH 1.0, minutes | 62 | 93 | 89 |

The number of leaves 112 on the #00 CC capsules 100 works the best around 12 pieces for a CC capsule 100 with a body portion 102 with modified release properties. The acid resistant properties of the CC capsule 100 peaks with 12 leaves 112 on the #00 CC capsules 100, indicating that the number of leaves 112 also affects the sealing of body portion 102 and its resistance to USP simulated gastric fluid. This may be due to the gap in the seal created by leaves 112 that are either too large or too fragmented.

The different disintegration times of body portion 102 and cap portion 104 give the CC capsule 100 a duo dissolution profile for its filling materials.

Example 7

Manufacturing CC capsules 100: heated size #00 body pin bars 202 are dipped into a cold capsule forming solution made of 20% hypromellose, 7% water soluble hypromellose acetate succinate and 73% water, and cap pin bars 204 are dipped into hypromellose solution made of 25% hypromellose and 75% water. After air tunnel drying to achieve a moisture level of 5-7%, CC capsules 100 are cut to size and pre-locked similar to regular hypromellose capsules for use.

A modified NJP-1200 encapsulation machine with all the modifications and running half the recommended speed of its maximum speed of 72,000 capsules per hour is used. The temperature of drying pin 500 is set to 43-48 degrees Celsius, and sealing pin 400 operates at room temperature, a sealing solution 412 made of 22% hypromellose, 7% of water soluble hypromellose acetate succinate, 0.1% xanthan gum and 70.9% water is used. Filling material for body portion 102 is canola oil, and filling material for cap portion 104 is white rice powder.

After filling, cut the closed end 105 of body portion 102 and set the CC capsule 100 upright such that the canola oil is on the topside for 1 hour to check for leaks. Besides normal disintegration of the whole filled capsules, 3 body portions 102 of filled CC capsules 100 are subjected to USP <701> basket dissolution testing method in simulated gastric fluid (SGF) with pH set to 1.0. Results are shown below.

| No. of Leaves/capsule | 8 pieces | 12 pieces | 16 pieces |
|---|---|---|---|
| Running Speed | 36,000 per hour | 36,000 per hour | 36,000 per hour |
| Moisture of CC capsule | 5.5% | 5.5% | 5.5% |
| Success rate | 91.1% | 99.4% | 96.2% |
| Cap cavity disintegration minutes | 4 | 7 | 5 |
| Body cavity intact in USP simulated gastric fluid pH 1.0, minutes | 74 | 92 | 86 |

The speed of the liquid filling process does not alter the choice of optimum number of leaves 112 on the #00 CC capsules 100. The best results are achieved with 12 leaves 112 on a #00 CC capsule 100.

An advantage of the embodiments previously described is that both the filling process and encapsulation process for the CC capsule 100 can all be done in one continuous process. This eliminates the need for multiple processing steps and increases cost-effectiveness for the use of CC capsule 100.

Another advantage of the embodiments previously described is that the modifications needed to produce CC capsules 100 using current industrial automatic dipping machines are very minimal. Only slight changes are needed that will not slow down or change the normal continuous operational procedures for the dip-moulding machines. Therefore, mass production of CC capsules 100 can be achieved without significantly altering the efficiency and costs structure for manufacturing traditional hard shell capsules.

The embodiments described in this document provide non-limiting examples of possible implementations of the present technology. Upon review of the present disclosure, a person of ordinary skill in the art will recognize that changes may be made to the embodiments described herein without departing from the scope of the present technology. Yet further modifications could be implemented by a person of ordinary skill in the art in view of the present disclosure, which modifications would be within the scope of the present technology.

What is claimed is:

1. A compartmented hard shell capsule for containing active formulations, the compartmented hard shell capsule comprising:
   a cap portion having a hollow cavity defining a cap chamber; and
   a body portion removably inserted into the cap portion, the body portion having an open end, a closed end and a sidewall defining a hollow cavity and a foldable serrated edge along the open end, said foldable serrated edge foldable to enclose the open end;
   wherein the foldable serrated edge forms a barrier to enclose the body portion, thereby creating a body chamber that is separate from the cap chamber when the body portion is inserted into the cap portion.

2. The compartmented hard shell capsule of claim 1, wherein
   the foldable serrated edge comprises of a plurality of triangle-shaped flaps projecting from the open end, the plurality of triangle-shaped flaps having overlapping edges when folded over to form the barrier.

3. The compartmented hard shell capsule of claim 1, wherein
   the foldable serrated edge is bent inwards towards the center of the body portion.

4. The compartmented hard shell capsule of claim 3, wherein
   the foldable serrated edge is bent inwards at an angle of about 1 to 10 degrees.

5. The compartmented hard shell capsule of claim 4, wherein
   the foldable serrated edge is bent inwards at an angle of about 2 to 3 degrees.

6. The compartmented hard shell capsule of claim 1, wherein the cap portion is comprised of a different material composition from that of the body portion.

* * * * *